(12) United States Patent
Mett

(10) Patent No.: US 7,935,234 B2
(45) Date of Patent: May 3, 2011

(54) ELECTROCHEMICAL GAS SENSOR AND PROCESS FOR MANUFACTURING SAME

(75) Inventor: Frank Mett, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 1688 days.

(21) Appl. No.: 11/120,348

(22) Filed: May 2, 2005

(65) Prior Publication Data

US 2006/0021873 A1    Feb. 2, 2006

(30) Foreign Application Priority Data

Jul. 31, 2004   (DE) .......................... 10 2004 037 312

(51) Int. Cl.
*G01N 27/26*    (2006.01)
(52) U.S. Cl. ........ 204/412; 204/400; 204/194; 204/401; 73/31.01
(58) Field of Classification Search .................. 204/194, 204/400–401, 406, 409–412, 424, 435; 73/31.01
See application file for complete search history.

(56) References Cited

U.S. PATENT DOCUMENTS

| | | | | |
|---|---|---|---|---|
| 4,961,834 A * | 10/1990 | Kuhn et al. | ..................... | 204/412 |
| 5,719,325 A | 2/1998 | Kiesele et al. | | |
| 6,376,124 B1 * | 4/2002 | Dodgson et al. | .............. | 429/127 |
| 6,924,059 B1 * | 8/2005 | Kawakami et al. | ........... | 429/162 |
| 2002/0194820 A1 * | 12/2002 | Jones | ............................. | 53/441 |
| 2003/0040785 A1 * | 2/2003 | Maschino et al. | ............. | 607/118 |
| 2004/0033414 A1 * | 2/2004 | Rohrl | .............................. | 429/46 |
| 2004/0128823 A1 * | 7/2004 | Mole | ............................ | 29/592.1 |

FOREIGN PATENT DOCUMENTS

| | | |
|---|---|---|
| DE | 195 47 150 | 6/1997 |
| DE | 195 47 150 A1 | 6/1997 |
| DE | 197 47 875 A1 | 5/1999 |
| EP | 1 413 881 A2 | 4/2004 |
| GB | 2 067 764 A | 7/1981 |
| GB | 2 386 955 | 10/2003 |
| WO | WO 88/09500 | 12/1988 |

OTHER PUBLICATIONS

Cammann K., Glaster H.; "Das Arbeiten mit ionenselektiven Elektroden"; 3. Auflage, 1996; Springer Verlag, S. 222f.

* cited by examiner

*Primary Examiner* — Nam X Nguyen
*Assistant Examiner* — Bach T Dinh
(74) *Attorney, Agent, or Firm* — McGlew and Tuttle, P.C.

(57) ABSTRACT

A planar electrochemical gas sensor is provided with at least one working electrode (4), at least one counterelectrode (4"), at least one electrolyte-filled planar electrolyte carrier (10), at least one planar housing upper part (3) and at least one planar housing lower part (2). The electrodes (4, 4") are arranged such that they are in two-dimensional contact with the electrolyte carrier (10). The housing upper part (3) and the housing lower part (2) are connected with one another such that the electrodes (4, 4") and the electrolyte carrier (10) are pressed against one another in such a way that they are secured against displacement. The housing upper part (3) and the housing lower part (2) are partially in direct two-dimensional contact with one another, and the connection of the housing upper part (3) and the housing lower part (2) in the area of the direct two-dimensional contact is present at least along a closed figure, which surrounds the electrodes (4, 4") and the electrolyte carrier (10).

25 Claims, 2 Drawing Sheets

ELECTROCHEMICAL GAS SENSOR AND PROCESS FOR MANUFACTURING SAME

CROSS REFERENCE TO RELATED APPLICATIONS

This application claims the benefit of priority under 35 U.S.C. §119 of German Application DE 10 2004 037 312.4 filed Jul. 31, 2004, the entire contents of which are incorporated herein by reference.

FIELD OF THE INVENTION

The invention relates generally to electrochemical gas sensors and more particularly to electrochemical gas sensors that are less bulky and to a process for easily assembling such electrochemical gas sensors.

BACKGROUND OF THE INVENTION

Electrochemical gas sensors are suitable for detecting chemical components in gases. Possible uses of gas sensors according to the present invention are found in fields of use of conventional electrochemical gas sensors as well as in fields of use in which the use of such sensors has not hitherto been possible for reasons related to size.

Due to their principle of action, electrochemical gas sensors contain a plurality of electrodes, which communicate with one another via an electrolyte. The arrangements used most commonly comprise a working electrode and a counterelectrode or a working electrode and a counterelectrode, with which a reference electrode is associated.

Electrochemical gas sensors currently comprise usually a large number of components, which are arranged piece by piece in mostly injection-molded plastic housings in a plurality of operations. Among other things, the above-mentioned electrodes, which are wetted by electrolyte at least on one side and are often even completely enclosed by electrolyte, are arranged in the housing. Due to the relatively large minimum electrolyte volume needed to wet all electrodes and the hygroscopic properties of most electrolytes, a large compensation volume must be provided in the prior-art designs in order to cover the broadest possible range of environmental humidity levels and to prevent as a result the sensor from bursting or drying out. Requirements applicable to the height and a minimum volume of prior-art sensor designs arise from the requirements imposed on the electrolyte volume as well as other general design conditions concerning the assembly of a plurality of components. Thus, the size of these sensors hinders the further spread of the use of electrochemical gas sensors despite the possibility of the adequately reproducible measurement of a great variety of gas components.

Another drawback of prior-art electrochemical gas sensors is the great effort that is needed for their assembly.

It is known from DE 195 47 150 A1 that the volume of an electrochemical gas sensor can be reduced by using as the electrolyte volume the volume of electrolyte that can be placed into a planar electrolyte carrier. The electrodes necessary for the ability of the electrochemical gas sensor to function are arranged around the electrolyte carrier. These are covered by gas-permeable membranes. The sandwich-like arrangement is surrounded by a planar upper part and lower part, which form a housing. It is explicitly stated here that strength is imparted to the housing by a circumferential frame. The relatively complicated structure of the housing remains as a possibly limiting drawback in the above-described embodiment.

It is, furthermore, known that a pocket structure, which accommodates the corresponding sensor components, can be formed by the frameless connection of the approximately planar upper and lower parts (EP 1 413 881 A2). The drawback of the solution being presented here is, however, that the electrodes are contacted by the connection area between the housing parts. Even though the structure of the initial porous contact material is changed during the connection of the housing parts such that the diffusion of the electrolyte is greatly reduced, experience has shown that it is not possible to find a solution that would be stable over the long term in this manner.

SUMMARY OF THE INVENTION

The basic object of the present invention is to provide an electrochemical gas sensor that is less bulky and can be assembled easily, which can be assembled from a small number of individual components, has long-term stability and whose mechanical design permits its use in a broad range of environmental humidities.

The present invention is based on the fact that it is possible to further simplify planar sensor structures. Planar electrodes and planar electrolyte carriers can be combined such that they have, on the whole, geometrically smaller dimensions than the housing surrounding the planar electrodes and the planar electrolyte carriers. If they are embedded in a sandwich-like manner in a housing structure that comprises a housing upper part and a housing lower part, it becomes possible, if the housing parts have sufficiently large dimensions, to allow areas of the housing parts to come directly into contact. Simple connection mechanisms can thus be used to connect the housing upper part with the housing lower part and to encapsulate the structure comprising electrodes and electrolyte carrier. It was found that sufficient strength and flexural strength of the sensors according to the present invention can thus be achieved without the additional need for circumferential frame structures for reinforcement. The use of surface areas that are in contact with each other between the housing upper part and the housing lower part makes possible a large number of especially simple assembly variants. Any escape of electrolyte is prevented from occurring with certainty at least in the connection area between the housing parts if the housing parts are connected along a closed figure, which encloses all other components of the sensor, and contact paths are not led through the connection area.

The requirements that are imposed on the material of the housing are the inert character of this material to ensure that no interactions will take place with the electrolyte or the electrodes; an at least noncontinuous electric volume conductivity in order to allow the electrodes to communicate with one another exclusively via electrolytes and to avoid short-circuits; a low minimum flexibility due to the nature of the construction at least during the connection of the housing upper part and the housing lower part, as well as availability at a low cost. These requirements are met in an excellent manner by numerous planar materials, especially plastics, but also thin glasses. These materials can also be processed, their dimensions can be changed, and they can be provided with openings that may become necessary for electrochemical sensors before or after the assembly without problems.

A sensor according to the present invention is a planar electrochemical gas sensors with at least one working electrode, at least one counterelectrode, at least one planar electrolyte carrier filled with electrolyte, at least one planar housing upper part and at least one planar housing lower part, wherein the electrodes are arranged such that they are in two-dimensional contact with the electrolyte carrier, and the housing upper part and the housing lower part are connected with one another such that the electrodes and the electrolyte carrier are pressed against one another such that they are secured against displacement, the housing upper part and the housing lower part are partially in direct two-dimensional contact with one another, and the connection between the housing upper part and the housing lower part in the area of the direct two-dimensional contact is present at least along a closed figure, which surrounds the electrodes and the electrolyte carrier. In an advantageous embodiment, an additional electrode may be additionally comprised as a reference electrode, which is likewise in two-dimensional contact with the electrolyte carrier. Due to the fact that the housing parts are at least partially in two-dimensional contact with one another, advantageous processes can be used, as was mentioned, to connect the individual housing parts. This can be carried out, for example, by partially bonding, welding, adhesively connecting in another way or laminating against each other the housing parts in those areas in which they are in contact with each other. Housings that are circumferentially closed can thus be manufactured with a sandwich structure comprising an electrolyte carrier and electrodes, which sandwich structure is located on the inside. Sensors according to the present invention can be in contact with the environment through individual openings in the housing parts, just like commercially available sensors. Thus, contacts with electrode surfaces and contact pads, which are in turn in contact with the electrodes, can thus be established via small openings in the housing parts.

So-called liquid seals are especially suitable for sealing the interior space of the sensor against contact areas accessible from the outside. These consist, for example, of chemical-resistant resins, greases or adhesives. An essential property of the materials used as a liquid seal is their good wetting behavior. As a result, they stop creep processes of various electrolytes and prevent their escape. Epoxy resins without curing agent, silicone-based high-vacuum grease or high-vacuum grease based on polytetrafluoroethylene have proved to be especially advantageous materials.

The diffusion of the gases to be detected to the working electrode may take place by permeation through the housing. In an advantageous embodiment, in which an opening is located in the housing in the vicinity of the working electrode, which opening is closed by a membrane that is permeable at least to the substance to be detected, the gases to be detected can enter through this opening. Furthermore, it is advantageous to keep the other electrodes in contact with atmospheric oxygen at least via small openings in the housing. The changes in the volume of the mostly hygroscopic electrolytes, which are caused by variations in the environmental humidity, impose only slight design requirements due to the small electrolyte volumes.

The nature of the sensor becomes nearly independent from the environmental humidity if an ionic liquid is used as the electrolyte. Because of the fact that its vapor pressure is nonexistent or nonmeasurable, such a liquid does not escape even in an extremely dry environment, which leads to a very long service life of the sensors filled with such a liquid even in case of very small electrolyte volumes.

In an advantageous embodiment, the electrolyte can be filled into the electrochemical sensor through an opening in the housing, which can be sealed after the conclusion of the filling. The ability of the electrolyte carrier to be subsequently filled represents, for example, a great advantage when standardized gas sensors are manufactured, which are to be adapted to the particular intended use only shortly before their use.

As an alternative to this, it is possible to fill the electrolyte carrier, for example, in the form of a nonwoven, with the electrolyte already before the assembly and to assemble it subsequently in the filled state before the housing parts are sealed or connected. This variant offers great advantages especially in case of the use of so-called ionic liquids, because filling can also be carried out at greater time intervals in relation to the assembly proper, without having to accept changes in the saturation of the nonwoven during the storage or transport of the electrolyte carrier.

An especially advantageous group of materials for forming the housing parts are polymer films, especially thicker films, which have sufficient intrinsic rigidity. Above all, such films make possible the use of a highly effective manufacturing process for manufacturing the electrochemical gas sensors according to the present invention.

Such a process comprises at least the following steps:
1. arrangement of electrodes on a planar carrier as a housing lower part,
2. arrangement of a planar electrolyte carrier such that it covers the electrodes at least partially,
3. covering of the arrangement of carrier and planar electrodes and electrolyte carrier by another planar housing part as a housing upper part, and
4. subsequent connection of the housing parts with one another at points at which the housing upper part and the housing lower part can touch each other directly, the connection taking place at least along a closed figure, which surrounds the electrodes and the electrolyte carrier.

Before the housing parts are connected, the structure arranged according to the present invention is a sandwich structure of electrodes, electrolyte carriers and housing parts, in which larger free surfaces of the housing parts are located opposite each other. If pressure is applied to this structure at least at the points in which the housing parts are located directly opposite each other, the housing parts can be brought into contact with one another by elastic deformation. At least the housing upper part or the housing lower part will have an area in which it is elastically deformed between the area in which it is connected with the respective other housing part and the area in which there is a two-dimensional contact with the electrodes and/or the electrolyte carrier. The elastic restoring forces resulting from this are absorbed by the connection of the housing parts.

As a result, a force, which contributes to the fixation of the arrangement comprising the electrolyte carrier and the electrodes, is applied to the arrangement of the electrolyte carrier and the electrodes.

A structured film may be used to form the housing in especially advantageous embodiments, i.e., pre-embossed areas are present, which can accommodate electrodes and/or electrolyte carrier structures in a positive-locking manner and reduce the deformation necessary for the connection of the housing parts.

The housing parts that are in contact with one another can be connected with one another by corresponding pressing forces. Cold- or hot-forming systems may be used for this. The area can be bonded or welded to one another, connected with one another adhesively in another manner or, for example, laminated against each other by means of commercially available laminating devices.

It is advantageous for some connection methods to perform the activation of the surface of the surface areas of the housing that are located opposite each other before they are brought into contact with one another. This can be done in various ways, for example, by plasma activation or other photochemical or thermal methods.

If polymer films are used as the housing material, it is especially advantageous to mass-produce the housing parts as part of a film pocket that can be folded over, so that the arrangement of electrodes and electrolyte carrier must more or less only be wrapped into the film pocket before individual surface areas of the upper part and lower part are connected with one another. The process of manufacturing electrochemical gas sensors can thus be limited to a few process steps, so that gas sensors according to the present invention can be expected to be available at a low cost. Furthermore, the small dimensions of the gas sensors according to the present invention considerably expand the range of use of electrochemical gas sensors.

An interesting application arises against the background of the flat structure of the gas sensors according to the present invention wherever gas components are to be analyzed in gas flows, but a disturbance of the flow is to be extensively avoided. The flat sensors according to the present invention can be advantageously integrated in a flow-optimized component geometry.

The arrangement according to the present invention will be described in greater detail on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
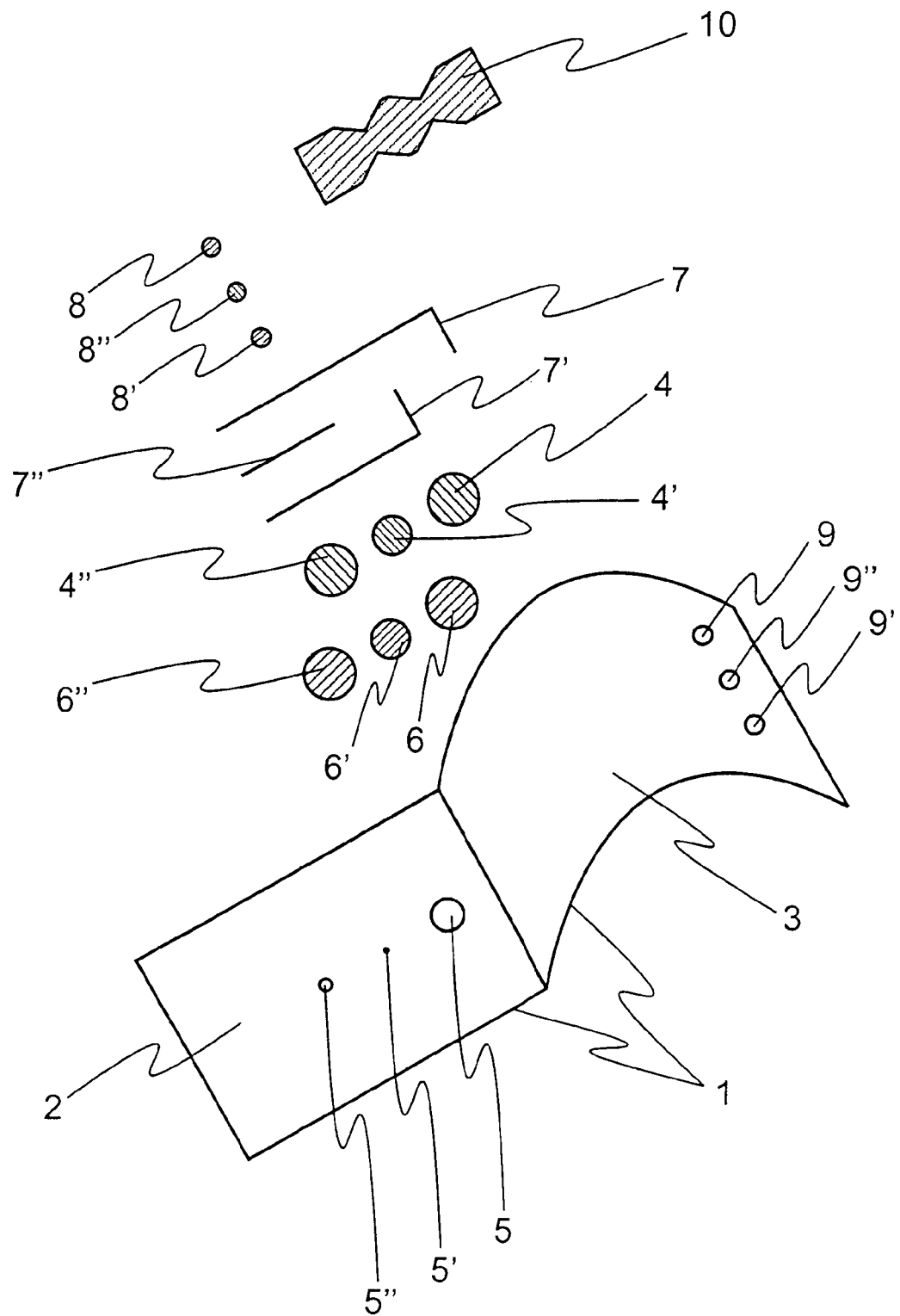
FIG. 1 is a schematic view of the sensor arrangement during assembly.

Referring to the drawings in particular, FIG. 1 shows a complete gas sensor according to the present invention in the form of an exploded view before assembly. It comprises a film pocket 1, comprising the later housing lower part 2 and the later housing upper part 3. Openings 5, 5', 5" are present in this film pocket 1 in the area of the housing lower part 2, above which the electrodes 4, 4', 4" are arranged, which can be used as a working electrode 4, a counterelectrode 4" and a reference electrode 4'. The largest opening 5 is used for the entry of the gas to be detected to the working electrode 4. The other openings 5' and 5" are used to supply the other two electrodes 4' and 4" with oxygen, the opening 5' for supplying the reference electrode 4' with oxygen being frequently eliminated. To prevent the electrolyte from escaping, the openings 5, 5', 5" are covered with membranes 6, 6', 6", which are permeable to the gas but are electrolyte-proof To avoid slipping during the assembly, these membranes 6, 6', 6" are mostly prefixed. This is achieved, for example, by using a prefabricated composite consisting of the material of the electrodes and the material of the membranes. If the electrode shapes needed are cut out of this composite, they are already connected with the corresponding gas-permeable membranes in such a way that they are secured against displacement.

Platinum wires acting as trip conductors 7, 7', 7" lead away from the electrodes 4, 4', 4" and to contact pads 8, 8', 8". The necessary potentials can be applied to the electrodes and measured signals generated can be tapped through openings 9, 9', 9" arranged in the housing upper part 3. The electrodes 4, 4', 4" are covered with a nonwoven structure as a planar electrolyte carrier 10. This nonwoven structure is placed on the electrodes 4, 4', 4" such that the electrode surfaces are covered by the electrolyte carrier 10 over their full area. Between the contact surfaces on the electrodes, the electrolyte carrier 10 has indentations, which act as compensating volumes in the plane of the electrolyte carrier 10 in the completely assembled sensor. To complete the sensor according to the present invention, the housing upper part 3 is folded over after all individual parts have been placed on the housing lower part 2. The entire arrangement thus wrapped into the film pocket 1 is led through a laminating device, as a result of which areas of the housing parts that are in contact with each other are laminated against each other and are connected with one another in this manner. A connection area of the housing, which extends along a closed figure, is formed now at least in the edge area of the sensor.

Figure 2:
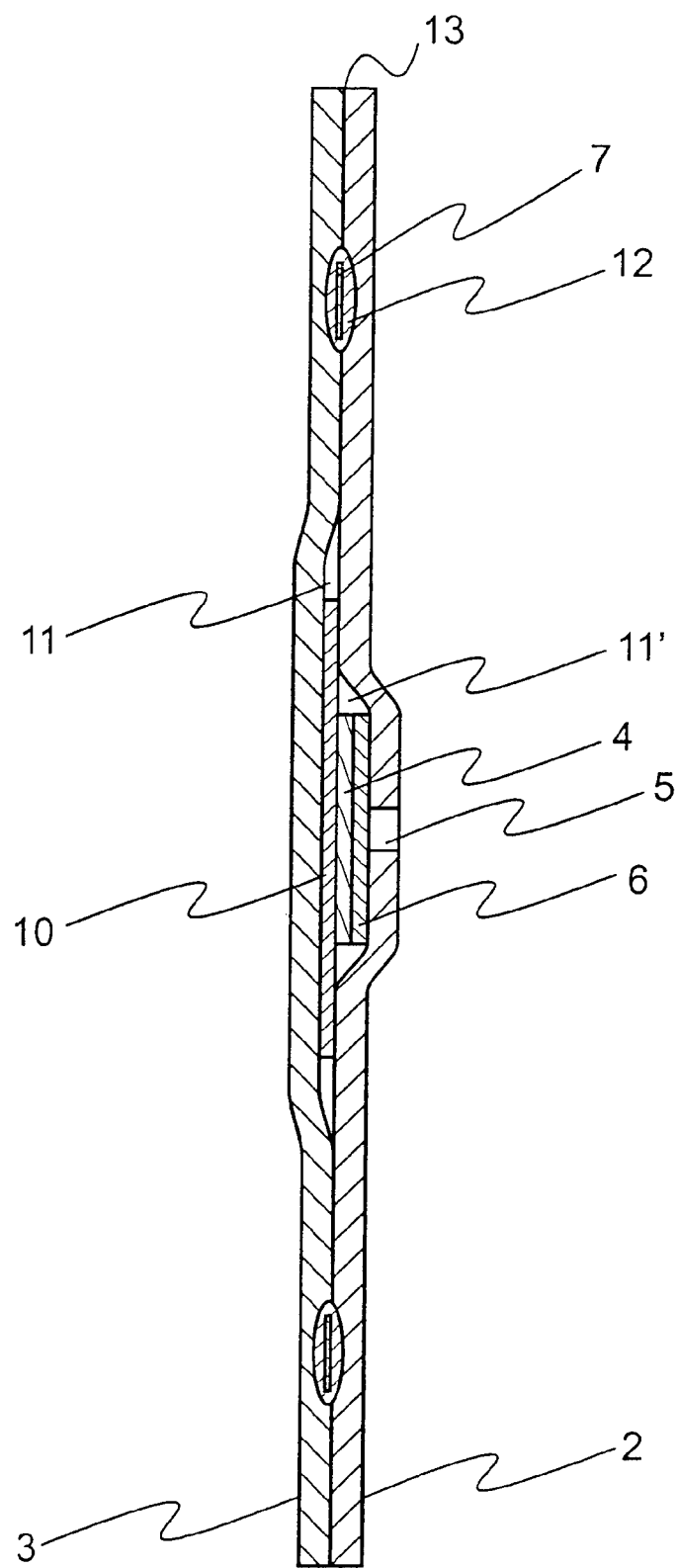
FIG. 2 is a sectional view of a completely assembled sensor according to the present invention.

FIG. 2 shows a sectional view of a completely mounted sensor according to the present invention. The gas-permeable membranes 6, electrodes 4 and electrolyte carrier 10 are arranged one on top of another and are embedded by the housing upper part 3 and the housing lower part 2.

The surfaces of the housing upper part 3 and the housing lower part 2 are directly in contact with one another in edge areas of the electrochemical sensor and are firmly connected with one another according to the present invention by lamination. In the areas in which electrodes 4 and/or electrolyte carrier 10 are located between the housing upper part 3 and the housing lower part 2, the housing parts are arranged at a certain distance from one another due to the construction. As a result, elastic deformation takes place during the connection of the housing parts, and the housing parts are pressed firmly onto the inner sandwich structure consisting of electrodes 4, gas-permeable membranes 6 and electrolyte carrier 10, as a result of which this structure is fixed in such a way that it is secured against displacement. Compensating volumes 11, 11', which are limited at least partially by the elastically deformed areas of the housing parts, are formed in the areas of the elastic deformation in the plane of the electrodes 4 and/or the electrolyte carrier 10 and/or the membrane 6, which is permeable to the substance to be detected. The housing parts connected with one another enclose, furthermore, small volumes 12, which are filled with a liquid seal. The strip conductors 7, which connect the electrodes with the contact pads, are led through these volumes 12. A connection area 13, in which the housing upper part 3 and the housing lower part 2 are directly connected with one another, is located at the edge of the sensor according to the present invention. This connection area contains no inclusions or passages and extends along a closed figure. As a result, no electrolyte can escape from the interior of the sensor through the connection area 13.

While a specific embodiment of the invention have been shown and described in detail to illustrate the application of the principles of the invention, it will be understood that the invention may be embodied otherwise without departing from such principles.

What is claimed is:
1. A planar electrochemical gas sensor, comprising:
a working electrode;
a counterelectrode;

an electrolyte-filled, planar electrolyte carrier;
a planar housing upper part with a planar surface; and
a planar housing lower part with a planar surface, said working electrode and said counterelectrode being arranged such that they are in two-dimensional contact with the electrolyte carrier in a two-dimensional contact region, said housing upper part and said housing lower part being connected with one another by said planar surfaces such that said working electrode and said counterelectrode and said electrolyte carrier are pressed against one another by said planar surfaces such that they are secured against displacement, said planar surface of said housing upper part and said planar surface of said housing lower part being partially in two-dimensional direct physical contact with one another with a connection between said planar surfaces of said housing upper part and said housing lower part being present in a direct two-dimensional housing part contact region entirely along a closed figure, which surrounds said working electrode and said counter electrode and said electrolyte carrier;

wherein said electrolyte in said electrolyte-filled electrolyte carrier has hygroscopic properties, said planar surfaces of said planar housing upper part and said planar housing lower part have elastically deformable areas which define a compensating volume and said electrolyte carrier has a plurality of indentations between said working electrode and counter electrode, said plurality of indentations of said electrolyte carrier also define said compensating volume.

2. A planar sensor in accordance with claim 1, further comprising a membrane permeable at least for the substance to be detected, wherein said planar housing upper part and said planar housing lower part define a housing with an opening closed in an electrolyte-proof manner with said membrane, said opening being provided in said housing in a vicinity of said working electrode.

3. A planar sensor in accordance with claim 1, wherein at least one of said housing upper part and said housing lower part has an area, between said housing part contact region and said two-dimensional contact region in which said at least one of said housing upper part and said housing lower part is elastically deformed and elastic restoring forces resulting therefrom are absorbed by said connection of the housing parts.

4. A planar sensor in accordance with claim 1, wherein said connection has an area in which the two housing parts are connected by lamination, bonding, welding or other adhesive techniques;
a reference electrode is in two-dimensional contact with the electrolyte carrier.

5. A planar sensor in accordance with claim 1, further comprising contact surfaces wherein said planar housing upper part and said planar housing lower part define a housing with openings and said electrodes are connected with said contact surfaces, said contact surfaces being disposed respectively relative to said openings in said housing for contact therewith from an exterior of said housing.

6. A planar sensor in accordance with claim 5, wherein said connection between said electrodes and said contact surfaces comprise electric lines, which lead at least partially through liquid seals arranged between said planar housing upper part and said planar housing lower part.

7. A planar sensor in accordance with claim 1, wherein said planar housing upper part and said planar housing lower part are made of a polymer film.

8. A planar sensor in accordance with claim 1, wherein said electrolyte carrier is filled with an ionic liquid.

9. A planar sensor in accordance with claim 1, wherein said housing upper part and said housing lower part enclose at least one compensating volume limited at least partially by elastically deformed areas of the housing parts, in the plane of the electrodes and/or the electrolyte carrier and/or a membrane permeable to the substance to the detected.

10. A process for manufacturing a planar electrochemical sensor, the process comprising the steps of:
arranging a planar working electrode and a planar counterelectrode on a planar surface of a housing lower part;
arranging a planar electrolyte carrier such that it at least partially covers the working electrode and the counterelectrode;
covering the arrangement of the electrolyte carrier, the housing lower part and the planar electrodes by a planar surface of a housing upper part;
forming a connection of the housing parts with one another at a region where the planar surface of the housing upper part and the planar surface of the housing lower part are directly in contact with each other, wherein the connection takes place entirely along a closed figure, which surrounds the electrodes and the electrolyte carrier;
wherein said electrolyte in said planar electrolyte carrier has hygroscopic properties, said planar surfaces of said housing upper part and said housing lower part have elastically deformable areas which define a compensating volume and said electrolyte carrier has a plurality of indentations between said planar working electrode and said planar counterelectrode, said plurality of indentations of said electrolyte carrier also define said compensating volume.

11. A process for manufacturing a planar sensor in accordance with claim 10, wherein a force is applied to the areas in which the connection is to take place to connect the housing upper part and the housing lower part.

12. A process in accordance with claim 10, wherein the housing parts to be connected with one another are one of laminated against one another, bonded or welded together or connected with one another adhesively in another way.

13. A process in accordance with claim 10, wherein the surface of the housing parts to be connected is activated before the housing parts are connected.

14. A process in accordance with claim 10, wherein parts of a film pocket, which can be folded over, are used as the housing upper part and said housing lower part, and the arrangement comprising the electrolyte carrier, the housing lower part and the planar electrodes is covered by folding over the parts of the film pocket that are used as the housing upper part.

15. A process in accordance with claim 10, wherein openings in the housing are prepared before the mounting of the individual parts of the sensor in the housing parts.

16. A process in accordance with claim 10, wherein before the electrodes are attached, an opening in the housing lower part is covered with a membrane, which is electrolyte-proof and is permeable to the substance to be detected.

17. A process in accordance with claim 16, wherein the electrolyte-proof membrane, which is permeable to the substance to be detected, is prefixed.

18. A process in accordance with claim 10, wherein the electrochemical sensor is filled with electrolyte through an opening in the housing.

19. A process in accordance with claim 18, wherein the opening through which the sensor is filled is sealed after the conclusion of the filling.

20. A process in accordance with claim 10, wherein the electrolyte carrier in the form of a nonwoven and is filled with the electrolyte before the assembly and is subsequently arranged in the filled state to cover the electrodes.

21. An electrochemical gas sensor, comprising:
a first housing having a planar surface;
a second housing having a planar surface;
a plurality of electrodes between said planar surfaces of said first and second housings;
an electrolyte-filled electrolyte carrier in contact with said plurality of electrodes and arranged between said planar surfaces of said first and second housings;
said planar surfaces of said first and second housings being in direct physical contact against each other entirely in a connection area which extends completely around said plurality of electrodes and said electrolyte carrier;
wherein said electrolyte in said electrolyte-filled electrolyte carrier has hygroscopic properties, said planar surfaces of the first and second housings have elastically deformable areas which define a compensating volume and said electrolyte carrier has a plurality of indentations between said plurality of electrodes, said plurality of indentations of said electrolyte carrier also defining said compensating volume.

22. A sensor in accordance with claim 21, wherein:
said first and second housings are of a size, shape and material to fix said plurality of electrodes and said electrolyte carrier against displacement relative to each other and said housings when said housings are connected to each other by said connection area.

23. A sensor in accordance with claim 21, wherein:
said plurality of electrodes and said electrolyte carrier are fixed against displacement relative to each other and to said housings by an elasticity of said housings when said housings are connected to each other by said connection area;
each of said plurality of electrodes are spaced from said connection area.

24. A sensor in accordance with claim 21, wherein:
said first housing includes an embossed area for accommodating one of said plurality of electrodes and said electrolyte carrier.

25. A sensor in accordance with claim 21, wherein:
one of said first and second housings are permeable to a gas that the electrochemical gas sensor senses.

* * * * *